United States Patent [19]

Clark et al.

[11] Patent Number: 6,156,809
[45] Date of Patent: Dec. 5, 2000

[54] MULTIPLE REACTOR SYSTEM AND METHOD FOR FISCHER-TROPSCH SYNTHESIS

[75] Inventors: Glen L. Clark, Katy; David G. Walker, Baytown, both of Tex.

[73] Assignee: Reema International Corp., Denver, Colo.

[21] Appl. No.: 09/295,989

[22] Filed: Apr. 21, 1999

[51] Int. Cl.[7] .............................. C07C 27/00; C07C 4/02
[52] U.S. Cl. ...................... 518/719; 518/703; 518/704; 518/705; 518/706; 585/752; 208/950
[58] Field of Search .................... 518/719, 703, 518/704, 705, 706; 585/752; 208/950

[56] References Cited

U.S. PATENT DOCUMENTS

| | | | |
|---|---|---|---|
| 2,632,017 | 3/1953 | Eastman et al. | 260/449.6 |
| 4,423,265 | 12/1983 | Chu et al. | 585/322 |
| 4,481,305 | 11/1984 | Jorn et al. | 518/705 |
| 4,579,985 | 4/1986 | Minderhoud et al. | 585/310 |
| 4,624,968 | 11/1986 | Kim et al. | 518/707 |
| 4,833,170 | 5/1989 | Agee | 518/703 |
| 5,348,982 | 9/1994 | Herbolzheimer et al. | 518/700 |
| 5,543,437 | 8/1996 | Benham et al. | 518/700 |
| 5,763,716 | 6/1998 | Benham et al. | 585/315 |

FOREIGN PATENT DOCUMENTS 0 823 470 A1  11/1998  European Pat. Off. .

OTHER PUBLICATIONS

Ajoy Raje et al, Fuel (1997), 76 (3), 273–280, Aug. 1997.

*Primary Examiner*—Johann Richter
*Assistant Examiner*—J. Parsa
*Attorney, Agent, or Firm*—Marsh Fischmann & Breyfogle LLP

[57] ABSTRACT

A Fischer-Tropsch process is provided for synthesizing hydrocarbons, involving multiple Fischer-Tropsch reactor stages (110) arranged in series, and characterized by very low carbon monoxide conversion per Fischer-Tropsch reactor stage (110) and intermediate removal of water between reactor stages (110). In one embodiment, the system utilizes an iron-based catalyst and balances the molar $H_2/CO$ feed ratio in the synthesis gas (108) with the overall $H_2/CO$ consumption ratio across all of the Fischer-Tropsch reactor stages (110). In a preferred embodiment, carbon dioxide is recycled from the last in series of the Fischer-Tropsch reactor stages (110) to the synthesis gas generator (106). The system may advantageously utilize a gaseous hydrocarbon feed (102), such as obtained from natural gas, as feed for producing the synthesis gas (108).

36 Claims, 4 Drawing Sheets

MULTIPLE REACTOR SYSTEM AND METHOD FOR FISCHER-TROPSCH SYNTHESIS

FIELD OF THE INVENTION

The present invention relates in general to Fischer-Tropsch synthesis of hydrocarbons from synthesis gas and, in particular, to Fischer-Tropsch synthesis involving a plurality of staged Fischer-Tropsch reactors which may be operated in a manner that is especially advantageous when using a gaseous hydrocarbon feed, such as natural gas, that tends to produce hydrogen-rich synthesis gas.

BACKGROUND OF THE INVENTION

Fischer-Tropsch processing is a well known technique for synthesizing hydrocarbon products. In general, Fischer-Tropsch synthesis processes involves converting a synthesis gas including hydrogen and carbon monoxide to hydrocarbon products in the presence of a Fischer-Tropsch catalyst. The most commonly used Fischer-Tropsch catalysts are iron-based and cobalt-based.

A Fischer-Tropsch process is generally thought to involve a complex combination of reactions. Some important reactions include the following:

I. $2\ H_2 + CO \rightarrow -CH_2- + H_2O$

II. $H_2O + 3CO \rightarrow -CH_2- + 2CO_2$

III. $H_2O + CO \rightarrow CO_2 + H_2$

Reactions I and II produce hydrocarbon products. Reaction III, referred to as the water-gas shift reaction, does not produce hydrocarbon products. In Reaction I, hydrogen and carbon monoxide are consumed in a molar ratio of hydrogen to carbon monoxide ($H_2$/CO consumption ratio) of 2 to produce hydrocarbon products. Therefore, if Reaction I were the only reaction occurring during the Fischer-Tropsch synthesis, the $H_2$/CO consumption ratio in the process would be 2. The effect of Reactions II and III, however, is to reduce the $H_2$/CO consumption ratio.

Early Fischer-Tropsch work involved gasification of coal to form synthesis gas. Synthesis gas produced in this manner is typically lean in hydrogen, often having a molar $H_2$/CO ratio of only about 0.6 to 0.7. In this situation, because the synthesis gas includes such a low $H_2$/CO ratio, reduction of the $H_2$/CO consumption ratio caused by Reactions II and III was not detrimental. Rather, Reaction III was generally considered to be beneficial because it produced additional hydrogen. Consumption of carbon monoxide in Reaction III was not a problem due to the relative surplus of that component in the system relative to hydrogen.

More recently, there has been significant interest in the use of gaseous hydrocarbon feeds, such as natural gas and petroleum gas, as the feed material for producing synthesis gas. Synthesis gas produced from natural gas tends to be rich in hydrogen and lean in carbon monoxide, with a $H_2$/CO ratio that is typically 2 or greater. If only Reaction I were present during the Fischer-Tropsch synthesis, a $H_2$/CO ratio of 2 in the synthesis gas would be optimal because it would match the $H_2$/CO consumption ratio in Reaction I. Unlike the situation with synthesis gas produced by coal gasification, Reactions II and III are detrimental when operating with such a hydrogen-rich synthesis gas, because Reactions II and III consume disproportionately large quantities of carbon monoxide. Therefore, when operating with a hydrogen-rich synthesis gas, it would generally be desirable to promote Reaction I and suppress Reactions II and III.

Cobalt-based catalysts, which tend to promote Reaction I and suppress Reactions II and III, have been proposed as preferred catalysts for Fischer-Tropsch synthesis when operating with a hydrogen-rich synthesis gas. With cobalt-based catalysts, $H_2$/CO consumption ratios that approach 2 are readily achievable. One problem with cobalt-based catalysts, however, is that they are expensive. Another problem with cobalt catalysts is that during the Fischer-Tropsch synthesis they tend to produce substantial amounts of undesirable methane and other light hydrocarbons, as opposed to more desirable higher molecular weight hydrocarbon products.

Iron-based catalysts have also been proposed for use in Fischer-Tropsch processes operating with a hydrogen-rich synthesis gas. Iron catalysts are typically substantially less expensive than cobalt catalysts. Also, iron catalysts tend to promote production of the more desirable higher molecular weight hydrocarbon products. A significant problem with iron-based catalysts, however, is that they tend to operate at a low $H_2$/CO consumption ratio, due to the higher activity of iron catalysts for promoting Reactions II and III. Consumption ratios of less than 1.2 are typical. The result is that significant carbon in the system is lost as a carbon dioxide waste product, and there is a significant excess of unreacted hydrogen, which is also wasted. This requires additional methane and oxygen for synthesis gas generation to produce a given quantity of hydrocarbon products. The low $H_2$/CO consumption ratio has largely discouraged the use of iron-based catalysts in Fischer-Tropsch operations using hydrogen-rich feed, such as natural gas, to produce the synthesis gas.

Accordingly, there is a need for an improved Fischer-Tropsch process in which the inherent advantages of iron-containing catalysts for promoting higher molecular weight products can be realized without the excessive waste of carbon and hydrogen, especially when using a hydrogen-rich synthesis gas, such as is produced from a natural gas feed.

SUMMARY OF THE INVENTION

The present invention provides a Fischer-Tropsch method of hydrocarbon synthesis that permits much higher $H_2$/CO consumption ratios to be attained when using iron catalysts and that avoids excessive losses of carbon to waste products. The method of the present invention is, therefore, very desirable when processing a hydrogen-rich synthesis gas, such as may be produced from natural gas or other gaseous hydrocarbon feeds. In one aspect, the method of the present invention involves conducting the Fischer-Tropsch reaction as a staged process with multiple Fischer-Tropsch reactor stages arranged in series and with a very low conversion of carbon monoxide in at least one, and preferably in all, of the Fischer-Tropsch reactor stages. Carbon monoxide conversions are typically less than 70% for each reactor stage, and more preferably in a range of from about 40 to about 60% for each reactor stage. Each Fischer-Tropsch reactor vessel is preferably a slurry reactor, in which particles of the catalyst are in a slurry with high molecular weight hydrocarbon products of the Fischer-Tropsch synthesis.

A significant advantage of the present invention is that it significantly increases the $H_2$/CO consumption ratio for iron-based catalysts and, accordingly, also reduces the loss of carbon to the production of carbon dioxide, resulting in a larger quantity of hydrocarbon product from a given quantity of gaseous hydrocarbon feed. With the present invention, it has been found that when the carbon monoxide conversion in a Fischer-Tropsch reactor stage begins to significantly exceed 50%, the water-gas shift reaction (Reaction III) becomes increasingly more active. Therefore, when the carbon monoxide conversion is maintained at a low level in each reactor stage, the water-gas shift activity may be significantly reduced and it is possible to convert a higher percentage of carbon monoxide in the synthesis gas to hydrocarbon product. The invention requires at least two reactor stages in series, but because the invention involves such a low conversion per reactor stage, it is typically preferred to have at least three reactor stages in series to achieve an acceptable yield of the desired hydrocarbon products.

In a further refinement, the process of the present invention involves intermediate removal of water between Fischer-Tropsch reactor stages, so that the partial pressure of water in the reactor vessels is maintained at a relatively low level, further suppressing Reactions II and III and tending to further increase $H_2/CO$ consumption ratios. The intermediate water removal, in combination with the low carbon monoxide conversion per reactor stage, can result in a significant improvement in the overall $H_2/CO$ consumption ratio and accompanying reduction in the loss of carbon to carbon dioxide waste product. With the process of the present invention, a $H_2/CO$ consumption ratio of at least 1.5, and often significantly higher, can typically be attained when using an iron-based catalyst in a slurry reactor.

In one preferred embodiment of the process of the invention, further operational enhancement is available in which the process is controlled so that the $H_2/CO$ ratio in the synthesis gas feed and the overall $H_2/CO$ consumption ratio across all of the series of Fischer-Tropsch reactor stages will have approximately the same values, typically within about 0.2 of each other and preferably even closer. This control is typically accomplished by recycling carbon dioxide from the last reactor stage in the series to the synthesis gas production step. Recycling of the carbon dioxide to balance $H_2/CO$ feed and consumption ratios, in combination with other features of the process of the invention, conserves carbon in the system for ultimate conversion to hydrocarbon product and tends to lower the $H_2/CO$ feed ratio so that it is approximately equal to the overall $H_2/CO$ consumption ratio. The result is that the present invention can provide significant operating advantages through increased hydrocarbon product yield and increased energy conversion efficiency. When the process of the invention is operated in this manner, it is typically possible to produce $C_5+$ hydrocarbon products that include at least about 90% of the carbon originally contained in the gaseous hydrocarbon feed, and to operate with a high energy conversion efficiency, so that the $C_5+$ hydrocarbon products have a total heating value of at least about 65% of the total heating value of the gaseous hydrocarbon feed.

While the process of the invention may be operated using any Fischer-Tropsch catalyst, the invention is contemplated for use primarily with iron-based catalysts, due to the significant advantages attainable when using iron-based catalysts with the present invention. Furthermore, certain iron-based catalysts are particularly preferred. One preferred iron-based catalyst is a precipitated iron catalyst of a very fine particle size, typically no larger than about 60 microns. Not to be bound by theory, these very fine precipitated iron catalysts are believed to be advantageous over iron catalysts of a larger particle size, because it is believed that larger iron particles tend to trap and effectively immobilize water in interior pore spaces of the particles, which tends to promote Reaction II and consequently lowers the overall $H_2/CO$ consumption ratio of the reacting synthesis gas. In contrast, it is believed that with the use of the very fine precipitated iron catalysts, less water tends to become trapped in interior pore spaces of the catalyst particles, significantly suppressing Reaction II.

Other preferred iron-based catalysts for use with the process of the invention are a supported iron catalysts, comprised of a thin layer of iron deposited on a support material, such as silica, alumina or carbon. Because the catalytically active iron layer is thin, it is believed to have a low tendency to trap water in interior pore spaces and to thereby suppress Reaction II, in a manner similar to that noted above with respect to the very fine precipitated iron catalysts. A further advantage of using supported iron catalysts, however, is that a larger particle size can be used relative to precipitated iron catalysts. This larger particle size significantly simplifies separation of the catalyst particles from liquid hydrocarbon products produced during the Fischer-Tropsch synthesis.

BRIEF DESCRIPTION OF THE DRAWINGS

For a more complete understanding of the present invention, and the further advantages thereof, reference is now made to the following detailed description taken in conjunction with the drawings, in which.

DETAILED DESCRIPTION OF THE PREFERRED EMBODIMENT

In the following description, the present invention is set forth in the context of a staged reaction system oriented towards Fischer-Tropsch synthesis of hydrocarbons from synthesis gas generated from a natural gas or other gaseous hydrocarbon feed. While the process must include at least two Fischer-Tropsch reactor stages, the description herein is made primarily to the use of three Fischer-Tropsch reactor stages, but the same principles apply equally to the use of smaller and larger numbers of stages.

Figure 1:
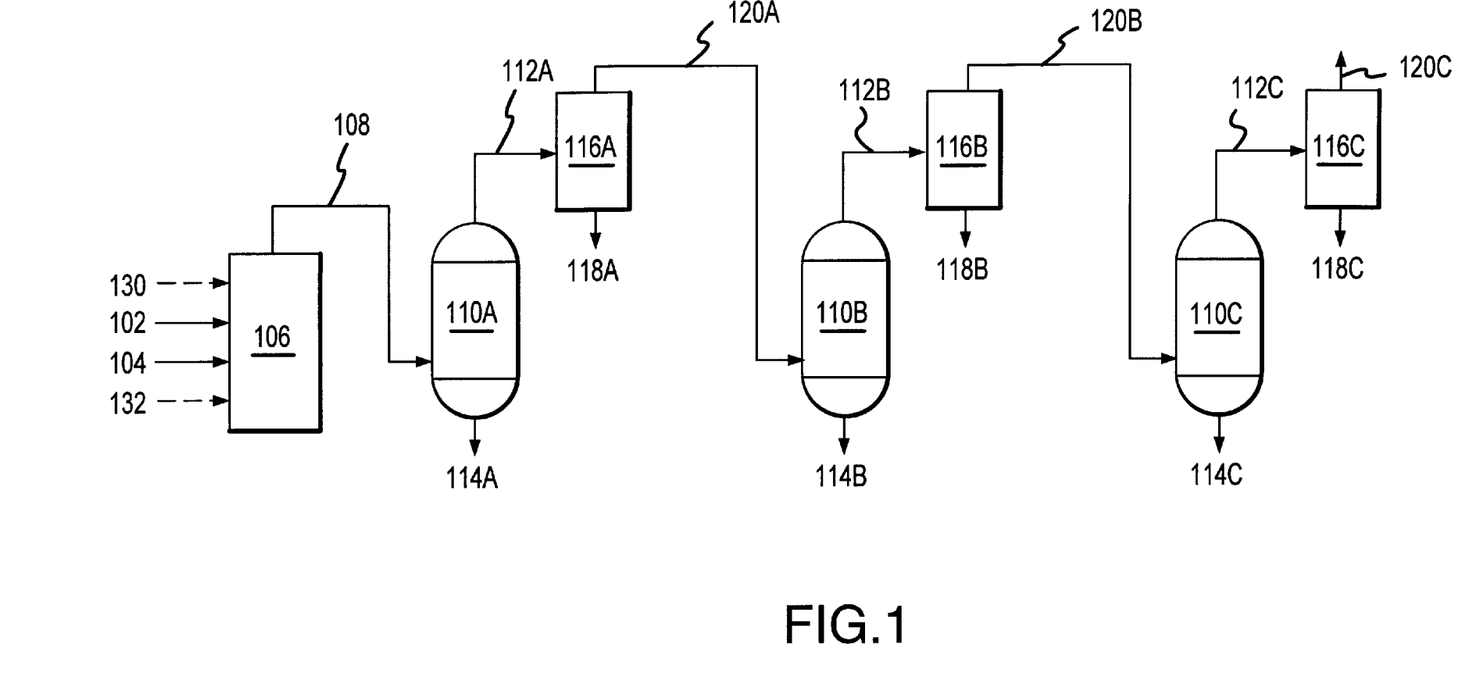
FIG. 1 is a process flow diagram (PFD) showing one embodiment of the Fischer-Tropsch hydrocarbon synthesis process of the present invention, including a synthesis gas generator and three Fischer-Tropsch reactor stages arranged in series.

Referring to FIG. 1, one embodiment of the Fischer-Tropsch process is shown in which a gaseous hydrocarbon feed 102 and oxygen gas 104 are fed to a synthesis gas generator 106, where synthesis gas 108 comprising hydrogen and carbon monoxide is generated. Although it is possible to add the oxygen gas 104 in the form of air, the use of a gas stream that is enriched in oxygen gas relative to air, such as may be produced by membrane separation of air, is preferred. Use of a gas stream enriched in oxygen gas reduces the need to process the large quantity of nitrogen present in air. The synthesis gas 108 is fed to the first in a series of three Fischer-Tropsch reactors 110 A, B and C. The Fischer-Tropsch reactors 110 A, B and C each have an internal reactor volume, containing a Fischer-Tropsch catalyst, where the Fischer Tropsch reaction occurs to produce Fischer-Tropsch reaction products, including the desired hydrocarbon products. The Fischer-Tropsch reactors 110 A, B and C, as shown in FIG. 1, are slurry reactors, meaning that catalyst particles are slurried in a liquid of high molecular weight hydrocarbons generated during the Fischer-Tropsch reaction. As synthesis gas passes through the slurry, hydrogen gas and carbon monoxide react to form hydrocarbon products.

The method of the invention is described with reference to the use of a gaseous hydrocarbon feed, such as natural gas, because such feeds are preferred and are particularly advantageous for use with the present invention, but it should be recognized that in its broadest scope the invention is not limited to such feeds. The method could also be advantageously used with other feed materials (such as coal, tars, bitumen, soot, and petroleum coke) from which synthesis gas could be produced. Furthermore, a combination of different types of feed could be used.

Each of the Fischer-Tropsch reactors 110 A, B and C shown in FIG. 1 represent a different Fischer-Tropsch reactor stage of the staged Fischer-Tropsch reaction. It should be recognized that each Fischer-Tropsch reactor stage could include one or more than one reactor vessel. When a stage includes more than one reactor vessel, the reactor vessels within the stage would be arranged in parallel, with each processing a different portion of feed to that stage. In the case of multiple reactor vessels in a stage, the total reactor volume for the stage would be the sum of the internal reactor volumes of all of the reactor vessels in the stage.

It should be noted that, as used herein, the term "Fischer-Tropsch reaction" does not refer to a single reaction, but to all reactions in a complex reaction system occurring in the reactors 110 A, B and C. In addition, it should be noted that the term "Fischer-Tropsch reaction products" includes all compounds resulting from the Fischer-Tropsch reaction taking place in the reactors 110 A, B and C. Fischer-Tropsch reaction products include, for example, hydrocarbon products, water and carbon dioxide. Furthermore, the "hydrocarbon products" referred to herein may include some quantities of oxygenated hydrocarbons, e.g., alcohols, ketones, aldehydes, etc. These oxygenated components, however, typically comprise only a small portion of the total hydrocarbon products, and preferably less than about 10 weight percent of the total hydrocarbon products.

Exiting each Fischer-Tropsch reactor 110 A, B and C are a gaseous effluent 112 A, B and C and a liquid effluent 114 A, B and C. Each of the liquid effluents 114 A, B and C includes heavier hydrocarbons, such as those of about $C_{11}$ and larger. Typically, a large portion of the each of the liquid effluents 114 A, B and C will be in the wax range. Each of the gaseous effluents 112 A, B and C includes lighter hydrocarbons, carbon dioxide, water and unconverted hydrogen and carbon monoxide. Each of the gaseous effluents 112 A, B and C is cooled and then is sent to a separator 116 A, B and C where condensed liquids 118 A, B and C are removed. Noncondensible gases 120 A and B from the first two reactors 110 A and B are fed to the next succeeding reactor in series, where unconverted hydrogen and carbon monoxide are reacted to form additional hydrocarbon products. The condensed liquids 118 A, B and C generally include water and liquid hydrocarbons, which are typically in a range of about $C_4$ to $C_{11}$. Because liquid hydrocarbons are a valuable product, they typically would be further separated from the water and recovered. The noncondensible gases 120 A, B and C generally include carbon dioxide, light hydrocarbons (typically about $C_4$ and smaller) and unconverted hydrogen and carbon monoxide.

As shown in FIG. 1, the noncondensible gases 120 A from the first Fischer-Tropsch reactor 110 A in series are fed to the second Fischer-Tropsch reactor 110 B in series. The noncondensible gases 120 B from the second Fischer-Tropsch reactor 110 B in series are fed to the third Fischer-Tropsch reactor 110 C in series. Accordingly, except for the last reactor in series, the unconverted hydrogen and carbon monoxide from each previous Fischer-Tropsch reactor is sent to the next succeeding Fischer-Tropsch reactor in the series.

An important aspect of the present invention is operation of the process with a low carbon monoxide conversion to Fischer-Tropsch reaction products in at least one, preferably two, and more preferably all three of the Fischer-Tropsch reactors 110 A, B and C. As used herein, the term "carbon monoxide conversion" means the molar percentage of carbon monoxide that reacts to form Fischer-Tropsch reaction products. The carbon monoxide conversion in a single reactor may be determined by comparing the quantity of carbon monoxide fed to the reactor with the quantity of carbon monoxide exiting the reactor, the difference representing the quantity of carbon monoxide converted. For example, if 100 moles of carbon monoxide is fed into a reactor and 40 moles of carbon monoxide exits the reactor, then the carbon monoxide conversion for that reactor would equal 60%. With the present invention, a low carbon monoxide conversion is considered to be a conversion percentage of no larger than 70%. Generally, however, enhanced performance with the process of the present invention is attained if the carbon monoxide conversion in one or more of the Fischer-Tropsch reactors is smaller than about 65%, with a carbon monoxide conversion of smaller than about 60% being more preferred. An especially preferred carbon monoxide conversion is in a range of from about 40% to about 60%, with around 50% being particularly preferred. In most instances, the carbon monoxide conversion will be at least about 40%.

A low carbon monoxide conversion in a Fischer-Tropsch reactor may be obtained by controlling operating conditions accordingly. In particular, it is generally desirable to have a short residence time in the reactor to prevent carbon monoxide conversion in the reactor from becoming too high. With the present invention, surprisingly, it is found that water-gas shift activity appears to be significantly suppressed at low carbon monoxide conversion rates. In particular, the water-gas shift activity appears to increase dramatically as the carbon monoxide conversion becomes significantly larger than about 50%. Above 70% carbon monoxide conversion, the water-gas shift activity becomes too high to obtain the benefits of low water-gas shift activity according to the present invention.

A further aspect of the present invention is that, although the carbon monoxide conversion may be low for each reactor, there is a high overall conversion of carbon monoxide across all of the reactors. This high overall carbon monoxide conversion is typically at least about 80% and preferably at least about 85%, with overall carbon monoxide conversion of at least about 90% often being achievable. For example, if the carbon monoxide conversion for each of the three reactors is at a level of 50%, then the overall carbon monoxide conversion rate will be 87.5%.

Although it is preferred that each of the Fischer-Tropsch reactors operate at a low carbon monoxide conversion, as noted above, the invention is not so limited. For example, one or more reactors could be operated at a low carbon monoxide conversion, below 70%, and one or more other reactors could be operated at a higher carbon monoxide conversion, above 70%. In this situation, it is desirable that at least the first reactor in the series of reactors be operated at the low carbon monoxide conversion. This is because the detrimental effects of high water-gas shift activity will typically be more detrimental in the first reactor than succeeding reactors. For this reason, it is preferred that at least the first reactor is operated at a carbon monoxide conversion of smaller than about 65%, and more preferably smaller than about 60%.

Another important aspect of the invention is the removal of water from each of the reactors, as is shown in FIG. 1. As noted above, water is removed from the gaseous effluent 112 A, B and C of each of the Fischer-Tropsch reactors in series 110 A, B and C in the separators 116 A, B and C. One reason for removing water is to reduce the degree to which water generated in a preceding reactor is available to participate in the water-gas shift reaction in a succeeding reactor. Intermediate removal of water between stages, therefore, suppresses Reactions II and III in succeeding reactors.

The combined effect of low carbon monoxide conversion per reactor and intermediate water removal is a relatively high hydrogen to carbon monoxide consumption ratio in each of the Fischer-Tropsch reactors, and also overall across all of the Fischer-Tropsch reactors, even when an iron-based catalyst is used. The hydrogen to carbon monoxide consumption ratio ($H_2$/CO consumption ratio) for a single reactor is the ratio of moles of hydrogen consumed in the reactor to the moles of carbon monoxide consumed in the reactor. This may be determined by comparing quantities of hydrogen and carbon monoxide fed to the reactor with quantities of hydrogen and carbon monoxide exiting the reactor, with the difference representing the quantity of each consumed. An overall $H_2$/CO consumption ratio across all of the Fischer-Tropsch reactors in series may be determined in a like manner by comparing quantities of hydrogen and carbon monoxide fed to the first reactor in series with the quantities of hydrogen and carbon monoxide exiting the last reactor in series. Frequently, each reactor is operated at approximately the same consumption ratio, in which case the overall $H_2$/CO consumption ratio will be approximately equal to the $H_2$/CO consumption ratios of the individual reactors. When iron-based catalysts are used with the present invention, the overall $H_2$/CO consumption ratio is controlled to be in a range having a lower limit of about 1.3, preferably about 1.4, more preferably about 1.5 and most preferably about 1.6 and having an upper limit of about 1.8 and preferably about 1.9. Most typical for the present invention is an overall $H_2$/CO consumption ratio in a range of from about 1.4 to about 1.8, with from about 1.5 to about 1.7 being even more typical.

The process of the present invention may be used with Fischer-Tropsch Periodic Table Group VIII catalysts other than iron-based catalysts, such as cobalt-based catalysts, although iron-based catalysts are preferred because they tend to produce a smaller percentage of light hydrocarbons and because iron-based catalysts are considerably less expensive. With the present invention, the tendency of iron-based catalysts to have high water-gas shift activity is significantly reduced with the process of the present invention. It is noted that, as used herein, an iron-based Fischer-Tropsch catalyst is any Fischer-Tropsch catalyst including iron as the predominant catalytic metal. The iron-based catalyst may, however, include lesser quantities of other materials, as are known in the art, such as copper, magnesium and potassium. In particular, a small quantity of potassium is preferred to promote higher molecular weight hydrocarbon products, as is known in the art. Preferred iron-based catalysts include from about 0.2 percent to about 20 percent copper, from about 0.2 percent to about 25 percent potassium, and from about 0 percent to about 30 percent magnesium, by weight relative to iron. Furthermore, the iron-based catalyst may be supported or unsupported.

In one embodiment of the present invention, it is possible to further enhance performance by balancing the molar feed ratio of hydrogen to carbon monoxide in the synthesis gas ($H_2$/CO feed ratio) with the overall $H_2$/CO consumption ratio. The $H_2$/CO feed ratio is the molar ratio of hydrogen to carbon monoxide in the synthesis gas feed to the first Fischer-Tropsch reactor in series. The overall $H_2$/CO consumption ratio is the same as described previously. Obtaining a good balance of the $H_2$/CO feed ratio and the overall $H_2$/CO consumption ratio, according to the invention, generally involves maintaining a high overall $H_2$/CO consumption ratio, as discussed previously, and controlling synthesis gas generation, such as by adding an appropriate amount of $CO_2$ and/or water during synthesis gas generation, to maintain a synthesis gas feed having a $H_2$/CO feed ratio approximately equal to the $H_2$/CO consumption ratio.

Referring again to FIG. 1, the synthesis gas generator 106 may apply any suitable technique for generating the desired synthesis gas, for example, partial oxidation, steam reforming, autothermal reforming or any combinations thereof. In the present invention, partial oxidation is preferred. The gaseous hydrocarbon feed 102 predominantly comprises normally gaseous hydrocarbons. As used herein, "gaseous hydrocarbon feed" includes feeds including at least some, and preferably comprising predominantly, normally gaseous light hydrocarbons (i.e., $C_4$–). The gaseous hydrocarbon feed may include some heavier hydrocarbon components (i.e., $C_5$+) and may include non-hydrocarbon components (such as nitrogen, helium, water, carbon dioxide and other carbon-containing compounds) although these non-hydrocarbon components are typically present in only small quantities. Typically, the hydrocarbon components of gaseous hydrocarbon feed 102 are comprised of at least 95 mole % of $C_4$– hydrocarbons, and more typically at least 99 mole % of $C_4$– hydrocarbons. In most instances, methane will be the predominant hydrocarbon component of the gaseous hydrocarbon feed 102. This would be the case, for example, when the gaseous hydrocarbon feed 102 is natural gas, and especially if LPG components (i.e., $C_3$ and $C_4$ components) are removed prior to synthesis gas generation. If the feed gas to the synthesis gas generator 106 comprises predominantly methane, then the $H_2$/CO ratio in the synthesis gas 108 produced by partial oxidation would typically be around 2. This is typically higher than a desired $H_2$/CO feed ratio for the present invention, because it tends to be higher than the $H_2$/CO consumption ratio of iron-based catalysts, even when operating at a high $H_2$/CO consumption ratio according to the present invention, as discussed previously. Therefore, control of the $H_2$/CO feed ratio generally involves reducing the $H_2$/CO ratio in the synthesis gas 108 below that which would normally result from partial oxidation of the gaseous hydrocarbon feed 102. As shown in FIG. 1, an optional addition of carbon dioxide 130 is shown to the synthesis gas generator 106. The effect of adding the carbon dioxide 130 is to reduce the $H_2$/CO feed ratio in the synthesis gas 108 to better match the overall $H_2$/CO consumption ratio across the Fischer-Tropsch reactors 110 A, B and C. The quantity of the carbon dioxide 130 should preferably be in an amount to provide the desired $H_2$/CO feed ratio in the synthesis gas 108.

With continued reference to FIG. 1, if the gaseous hydrocarbon feed 102 is from a natural gas that includes a naturally high carbon dioxide content, then part or all of the carbon dioxide 130 may be supplied as that naturally-occurring carbon dioxide in the gaseous hydrocarbon feed 102. Otherwise, the carbon dioxide 130 would have to be supplied separately, such as from flue gases or another source. FIG. 1 also shows optional addition of steam 132 to the synthesis gas generator 106, also for the purpose of adjusting the $H_2/CO$ feed ratio in the synthesis gas 108. The effect of adding the steam 132 is to increase the $H_2/CO$ ratio, such as may be desirable if the rate of addition of the carbon dioxide 130 is more than required to attain the desired $H_2/CO$ feed ratio.

In any reaction of methane with oxygen to make synthesis gas, the reaction is highly exothermic. In conventional processes, typically less than 75% of the heat of combustion of the gaseous hydrocarbon feed goes to heat of combustion of the synthesis gas. The rest of the heat of combustion of the gaseous hydrocarbon feed becomes sensible heat in the synthesis gas. If an optimum amount of steam and/or $CO_2$ is added to the reaction, the energy yield of synthesis gas from methane rises and can become as high as 90%. If this addition is primarily steam, the synthesis gas will contain a high $H_2/CO$ ratio. If, however, the additive is primarily carbon dioxide, the $H_2/CO$ ratio in the synthesis gas can be suppressed, typically to as low as about 1.4. The fraction of energy lost to sensible heat in the synthesis gas becomes less as does the synthesis gas temperature. The higher the energy efficiency of synthesis gas generation, the lower the amount of gaseous hydrocarbon feed and oxygen required to make a given quantity of synthesis gas.

Figure 2:
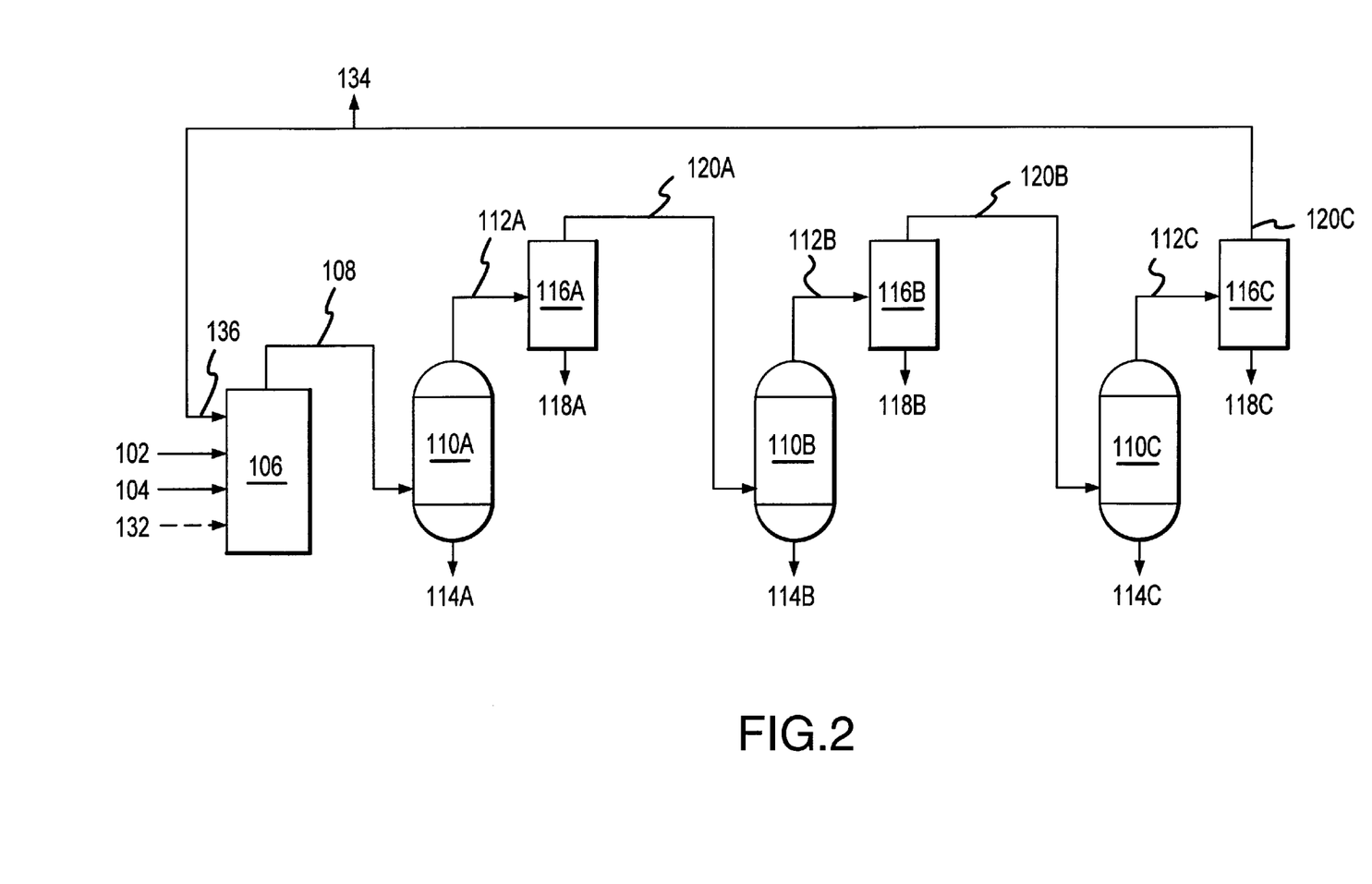
FIG. 2 is a PFD of another embodiment of the Fischer-Tropsch hydrocarbon synthesis process of the present invention, including carbon dioxide recycle to the synthesis gas generator.

A preferred source for carbon dioxide for use in synthesis gas generation is from recycle within the process, since carbon dioxide is produced as a Fischer-Tropsch reaction product. FIG. 2 shows one embodiment of the process of the present invention including carbon dioxide recycle. As shown in FIG. 2, a portion of noncondensible gases 120 C from the last Fischer-Tropsch reactor 110 C is recycled as a recycle stream 136 to the synthesis gas generator 106. As noted previously, the noncondensible gases 120 C include a significant quantity of carbon dioxide, as well as some light hydrocarbons produced during the Fischer-Tropsch reaction and unreacted hydrogen and carbon monoxide. A small bleed stream 134 is, however, removed to prevent an undesirable buildup of inert materials, such as nitrogen, in the system. Typically the bleed stream 134 is nor more than about 10% as large as the recycle stream 136. FIG. 2 also shows the optional addition of the steam 132.

Although FIG. 2 shows recycle of gases only from the last Fischer-Tropsch reactor 110 C, it should be recognized that recycle of a portion of one or more of the noncondensible gases 120 A and B from the first two Fischer-Tropsch reactors 110 A and B could be used instead of or in addition to recycle of the noncondensible gases 120 C. In a preferred embodiment, however, the recycle is substantially entirely from the last Fischer-Tropsch reactor 110 C, as is shown in FIG. 2. The noncondensible gases 120 A and B will necessarily include larger quantities of unreacted hydrogen and carbon monoxide than the noncondensible gases 120 C, and it is desirable to pass those unreacted components to the next reactor in series for further reaction to produce desired hydrocarbon products.

With the present invention, control of the $H_2/CO$ feed ratio in the synthesis gas through addition of carbon dioxide to the synthesis gas production step, combined with attainment of a high overall $H_2/CO$ consumption ratio across the Fischer-Tropsch reactors as described above, permits the $H_2/CO$ feed ratio and the overall $H_2/CO$ consumption ratio to be approximately matched to each other. With this embodiment of the present invention, the overall $H_2/CO$ consumption ratio can typically be controlled to be in a range of from about 0.2 smaller than to about 0.2 larger than the $H_2/CO$ feed ratio, preferably in a range of from about 0.15 smaller than to about 0.15 larger than the $H_2/CO$ feed ratio, more preferably in a range of from about 0.1 smaller than to about 0.1 larger than the $H_2/CO$ feed ratio, and most preferably in a range of 0.05 smaller than to about 0.05 larger than the $H_2/CO$ feed ratio. Typically, both the $H_2/CO$ feed ratio and the overall $H_2/CO$ consumption ratio are larger than about 1.3, preferably larger than about 1.4 and more preferably larger than about 1.5. Typically both the feed ratio and the overall $H_2/CO$ consumption ratio are smaller than about 1.9 and more typically smaller than about 1.8. A particularly preferred range for both the $H_2/CO$ feed ratio and the overall $H_2/CO$ consumption ratio is from about 1.4 to about 1.8, with a range of from about 1.5 to about 1.7 being even more preferred.

One significant benefit of the carbon dioxide recycle, as shown in FIG. 2, is that efficiency of conversion of the gaseous hydrocarbon feed 102 into the desired higher molecular weight hydrocarbon products is significantly enhanced. By balancing the $H_2/CO$ feed and consumption ratios, neither carbon monoxide nor hydrogen in the synthesis gas 108 are wasted in the large quantities that can result when an excess of one component is present. Furthermore, the synthesis gas 108 exiting the synthesis gas generator 106 will typically be an equilibrium gas composition including an equilibrium concentration of carbon dioxide. By recycling carbon dioxide, the equilibrium carbon dioxide concentration can be satisfied by the recycled carbon dioxide, rather than through consumption of fresh gaseous hydrocarbon feed 102. The result is that, with the high $H_2/CO$ consumption ratio of the present invention and the balancing of $H_2/CO$ feed and consumption ratios according to the present invention, a larger proportion of carbon from the gaseous hydrocarbon feed is typically incorporated into desirable higher molecular weight hydrocarbon products. Typically, $C_5+$ hydrocarbon products from the process of the invention will include at least about 85% of the carbon originally present in hydrocarbons of the gaseous hydrocarbon feed 102, and preferably at least about 90%. Furthermore, there is typically a high energy conversion efficiency in preparing hydrocarbon products from the gaseous hydrocarbon feed 102. Typically, with the process of the invention, the $C_5+$ hydrocarbon products will have a total heating value of at least about 65%, and preferably at least about 70%, of the total heating value of hydrocarbons in the gaseous hydrocarbon feed. In this regard, total heating value is determined for the $C_5+$ hydrocarbon products and the hydrocarbons of the gaseous hydrocarbon feed using the lower heats of combustion of the relevant components of each stream. The lower heat of combustion is a property of fuel materials determined by controlled combustion to form combustion products which include water, if at all, in the gaseous state. The lower heats of combustion for a number of materials are listed in Chemical Engineers' Handbook, 5th Ed. (McGraw-Hill 1973) at pages 3-145 through 3-147. To compare the total heating value of the $C_5+$ hydrocarbon products to that of the hydrocarbons in the gaseous hydrocarbon feed, the total heating value of a quantity of the $C_5+$ hydrocarbon products is compared to the total heating value of a corresponding quantity of gaseous hydrocarbon feed consumed to prepare the quantity of $C_5+$ hydrocarbon products.

As noted previously, the Fischer-Tropsch catalyst could be any Fischer-Tropsch catalyst effective for catalyzing the Fischer-Tropsch reaction. The preferred catalyst for use with the present invention, as discussed above, is an iron-based catalyst. Examples of suitable catalyst structures include precipitated catalysts, fused catalysts, sintered catalysts, cemented catalysts and supported catalysts. To further enhance performance of the process of the present invention, however, certain iron-based catalysts are preferred, and especially to promote a high $H_2/CO$ consumption ratio in the Fischer-Tropsch reactors.

The preferred iron-based catalysts have a structure that avoids the presence of significant deep pore spaces in the interior of the iron phase of the catalyst. This may be accomplished, for example, using either unsupported or supported iron-based catalysts. Unsupported iron catalysts will typically be made by precipitation as is known in the art. To avoid excessive deep pore volume in these unsupported catalysts, they should be limited to particles having a size of smaller than about 60 microns and preferably smaller than about 30 microns. Particle size may generally be determined by sieve analysis or, in the case of particles too small for sieve analysis, by other methods as are known for determining particle size. One problem with using such very fine catalyst particles is that they can be difficult to separate from hydrocarbon product due to the small particle size. Supported catalysts are typically made by precipitating a thin layer of catalytic iron material on small particles of a support material, as is known in the art. Typical support materials include inorganic oxides, and particularly ceramic materials, such as silica and alumina. Another support material is carbon. An advantage of using a supported catalyst is that larger catalyst particles may be used than for unsupported catalysts, which simplifies separation of catalyst particles from hydrocarbon product. When using a supported catalyst, the particles preferably have a size of larger than about 50 microns, and more preferably in a range of from about 50 microns to about 200 microns.

Not to be bound by theory, but to aid in the understanding of the invention, iron-based catalysts that avoid the inclusion of a significant amount of deep pore volume in the catalyst particles are believed to suppress Reaction II. In pore volumes deep within the catalytic iron, hydrogen and carbon monoxide can diffuse in and react at the catalyst surface inside the pore, producing water as a by-product. It is difficult, however, for the water to diffuse out of these deep internal pore volumes, with a result being that a high concentration of water builds up in the pore volume. As water builds up in the pore volume, Reaction II is promoted. By contrast, water produced at the exterior surface of the catalyst, or in interior pore volumes that are shallow and near the exterior surface, can more easily diffuse out and away from the catalyst, so that Reaction II does represent a problem of the same magnitude as in the deep pore volumes where the water must diffuse out and will likely contact chemisorbed carbon monoxide on its way to the gas phase, causing Reaction II to occur. In the very fine unsupported catalysts noted above, significant deep pore volume is avoided due to the small particle size. In the supported catalysts, the catalytic iron is present in only a very thin layer on the support and an excessive amount of deep pore volume in the catalytic layer is thus avoided.

Reactive conditions in the Fischer-Tropsch reactors may vary depending upon the specific operation, as is known generally in the art. When using iron-based catalysts, typical reactor temperatures are in a range of from about 210° C. to about 280° C., with lower temperatures generally promoting production of higher molecular weight hydrocarbon products. Typical operating pressures using iron-based catalysts in slurry reactors are from about 110 KPa to about 3500 KPa. With the present invention, operating pressures of from about 1000 KPa to about 4000 KPa are preferred. Furthermore, as is known in the art, catalyst compositions can be varied to promote different hydrocarbon products. For example, addition of a small amount of potassium to iron catalysts is known to promote production of higher molecular weight products.

Although other reactors, such as fixed-bed reactors or fluid bed reactors, could be used with the present invention, slurry reactors are preferred. Slurry reactors are preferred primarily because it is relatively easy to control the temperature in the reactor and the reactors are not highly susceptible to the development of hot zones in the reactor. The relative ease of temperature control is important due to the highly exothermic nature of the Fischer-Tropsch reaction. Temperature control is typically accomplished through the use of cooling tubes extending into the internal reactor volume in which the catalyst slurry is disposed during hydrocarbon synthesis.

One significant advantage of the present invention is the relative ease with which the reactors used to practice the process of the invention may typically be constructed and installed. Because the invention contemplates use of a plurality of staged reactors with relatively low conversion per reactor, it is often possible to keep the reactors small enough so that the reactors may be shop-fabricated and then transported to the field for installation. This is in contrast to the more conventional situation when a single reactor with a high conversion is used, often with the aid of large recycle volumes. Typically, such reactors are so large that transportation of the reactor is not feasible, necessitating expensive field fabrication. Also, with the present invention, the reactor volume required for each succeeding stage is typically less than the preceding stage, because throughput becomes smaller with each successive reactor stage. Preferably, each successive reactor stage has an internal reactor volume no larger than about 70% of the internal reactor volume of the immediately preceding reactor stage. This can result in a significant savings on reactor costs. The result is that even though the present invention uses multiple reactors instead of a single reactor, the multiple reactor system is typically cost competitive with single reactor designs.

The process could be conducted using reactor vessels that have decreasing reactor volumes in successive Fischer-Tropsch reactor stages. Preferably, however, reactor vessels of a single size and design could be used in all stages to further reduce capital costs. For example, in a three stage process, the first Fischer-Tropsch reactor stage could include three of the reactor vessels arranged in parallel, the second Fischer-Tropsch reactor stage could include two of the reactor vessels arranged in parallel and the third Fischer-Tropsch reactor stage could include only a single reactor vessel.

Furthermore, it should be recognized that the present invention has been described primarily with reference to the use of Fischer-Tropsch reactor stages that are each a physically separate unit, but the invention is not so limited. For example, the plurality of reactors could be provided as a single unit that is divided into separate reactor volumes, each acting as one of the plurality of reactor stages.

Figure 3:
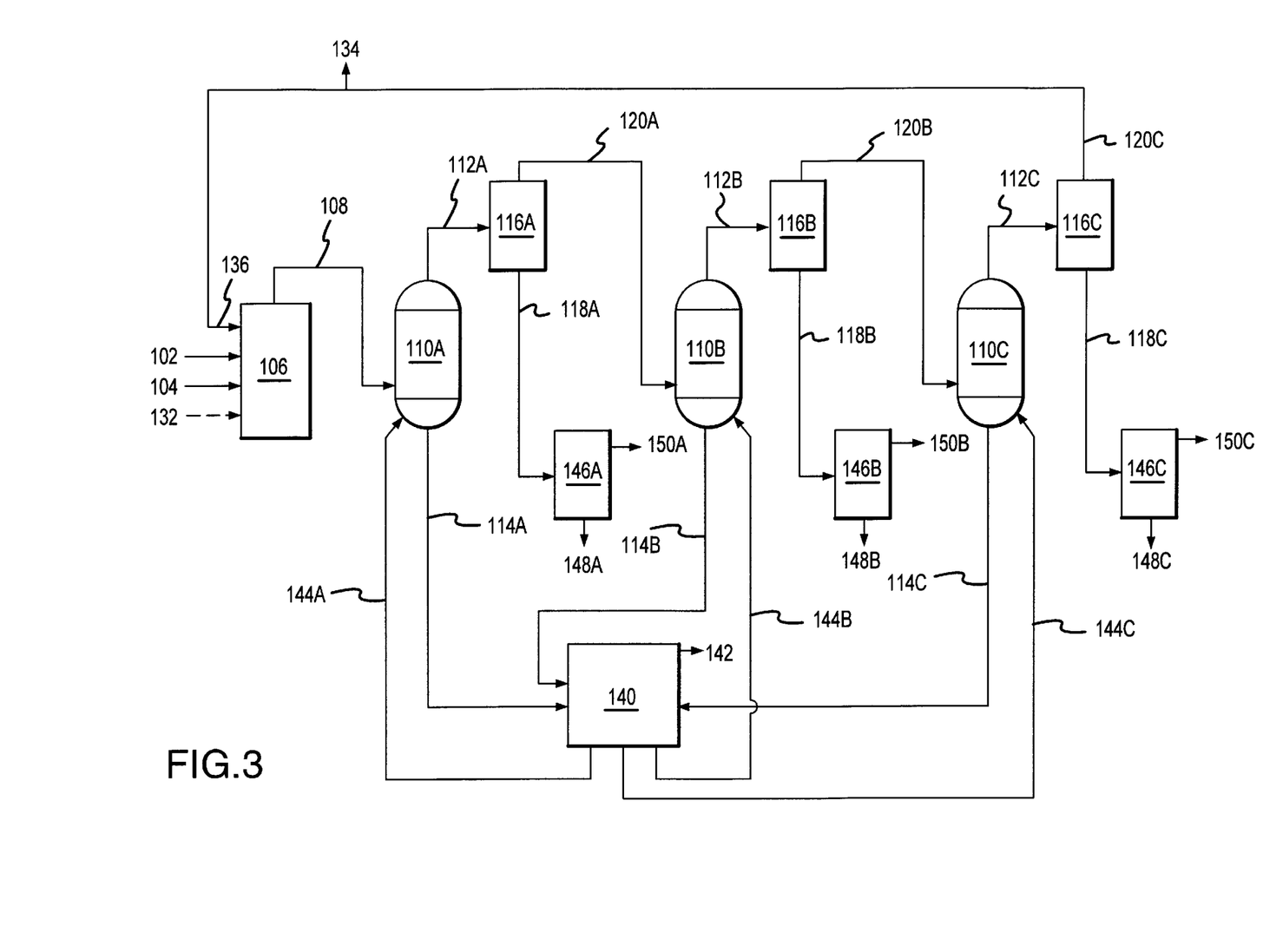
FIG. 3 is a PFD showing yet another embodiment of the Fischer-Tropsch hydrocarbon synthesis process of the present invention, including carbon dioxide recycle, hydrocarbon product recovery and catalyst separation and recycle.

One consideration with the use of slurry reactors is separation of catalyst particles from high molecular weight hydrocarbon product. FIG. 3 shows one embodiment of the process of the present invention including recovery of crude hydrocarbon products. As shown in FIG. 3, liquid effluents 114 A, B and C are withdrawn from each of the Fischer-Tropsch reactors 110 A, B and C. The liquid effluents 114 A, B and C each consists of a hot slurry of high molecular weight hydrocarbons and catalyst particles. Liquid effluents 114 A, B and C are each transferred to separation unit 140, where catalyst particles are separated to produce a crude wax product 142. The separation unit 140 could include one or a combination of a variety of separation methods, such as filtration, hydrocycloning, centrifuging, magnetic separation, or simple gravity settling. In a preferred embodiment, the separation unit 140 is a settling tank in which the catalyst particles are allowed to settle to the bottom and a crude wax product 142 is recovered. The separation unit 140 could include more than one settling tank, if desired. The crude wax product 142 contains a substantial quantity of high molecular weight hydrocarbons, generally from about $C_{11}$ to about $C_{100}$, or larger. Dense slurries 144 A, B and C of settled catalyst are withdrawn from the bottom of the settling tank 140 and returned to the Fischer-Tropsch reactors 110 A, B and C. A portion of the dense slurries 144 A, B and C may be removed and new catalyst added as required for periodic replacement of old catalyst with fresh catalyst. The dense slurries 144 A, B and C each have a high catalyst concentration, typically comprising from about 20 weight percent to about 60 weight percent of catalyst particles. This is in contrast to the catalyst concentration present in the Fischer-Tropsch reactors 110 A, B and C, in which the catalyst is in a slurry typically comprising from about 4 weight percent to about 30 weight percent of catalyst particles.

FIG. 3 also shows liquid separators 146 A, B and C which are used to separate water from light hydrocarbon liquids in the condensed liquids 118 A, B and C. The condensed liquids 118 A, B and C are fed to the corresponding liquid separators 146 A, B and C, where water 148 A, B and C is removed and light liquid hydrocarbons 150 A, B and C are recovered. The light liquid hydrocarbons 150 A, B and C typically include hydrocarbons from about $C_4$ to about $C_{11}$. The crude wax product 142 and the light hydrocarbon liquids 150 A, B and C could be sold individually or could be combined and sold as a single product. Alternatively, it is possible to upgrade these crude products into more valuable products. For example, crude wax product 142 could be purified to prepare a purified wax product.

Figure 4:
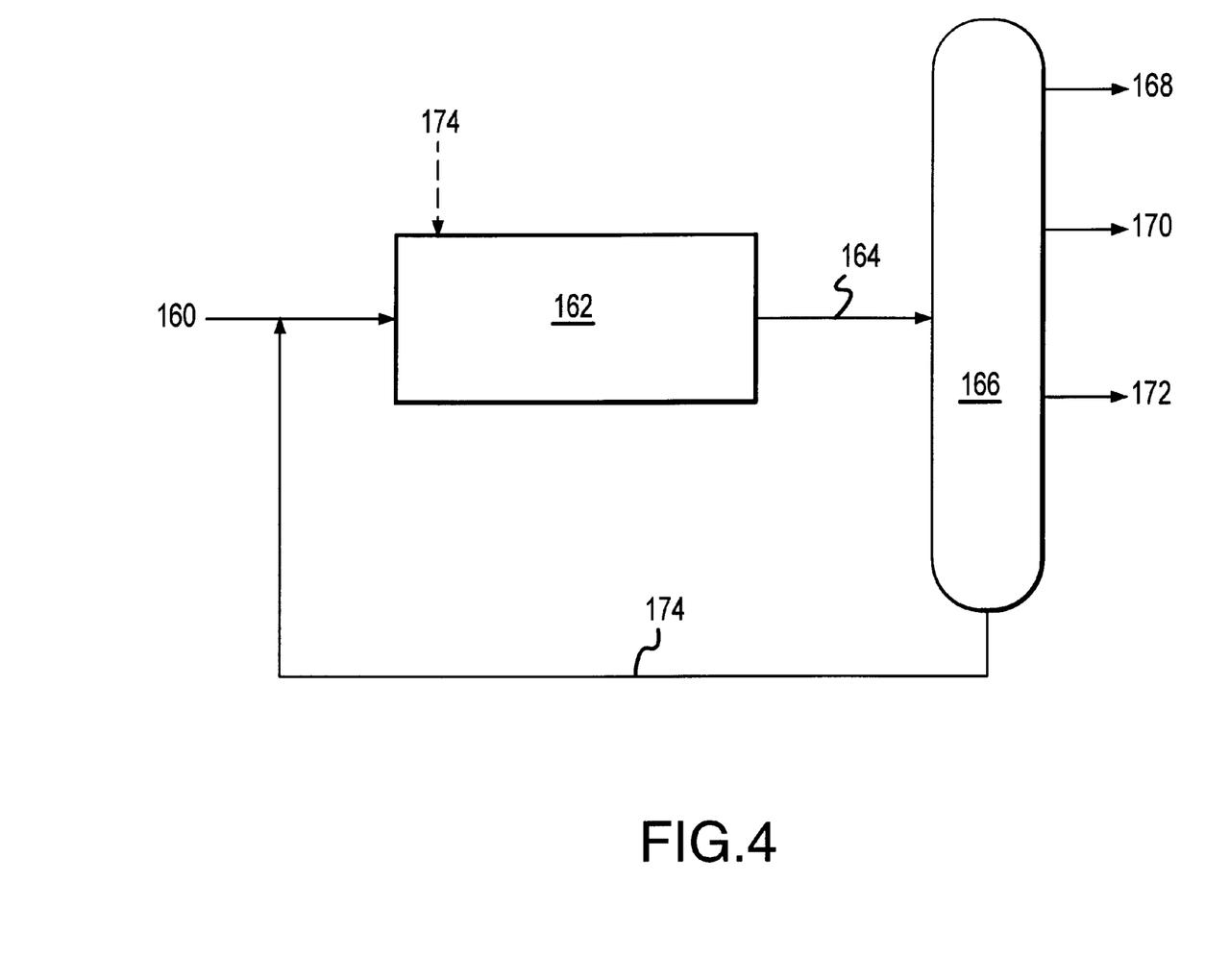
FIG. 4 is a PFD showing one embodiment of a product recovery operation for use with the Fischer-Tropsch hydrocarbon synthesis process of the present invention to convert crude synthesis product to distillate products.

In a preferred embodiment of the invention, it is contemplated that at least part of the crude hydrocarbon products will be converted to at least one distillate product, typically in at least one of the naphtha, jet fuel and diesel ranges. Referring now to FIG. 4, one embodiment for crude product upgrading is shown for preparing distillate products. In FIG. 4, a crude hydrocarbon feed 160 is fed to a cracking unit 162 to prepare a synthetic crude oil 164. The synthetic crude oil 164 itself could be a saleable product, but in the embodiment shown in FIG. 4, it is sent to a distillation unit 166. In the distillation unit, the synthetic crude oil 164 is distilled to make three distillate products, a naphtha range product 168, a jet fuel range product 170 and a diesel range product 172. Tower bottoms 174 are recycled back to the cracking unit 162. The distillate products 168, 170 and 172 are highly paraffinic and make excellent blending stocks for blending with conventional petroleum distillate products. As an example, the jet fuel range product 170 could be blended with conventional jet fuel refined from petroleum. As another example, the diesel range product 172 could be blended with conventional diesel fuel refined from petroleum. Also, the naphtha range product could be blended with conventional gasoline range products refined from petroleum. Other distillate products could also be produced, such as in the lubricating oil range.

The crude hydrocarbon feed 160, as shown in FIG. 4, includes at least a portion of the crude wax product 142 (as shown in FIG. 3) and may also include some or all of the light hydrocarbon liquids 150 A, B and C (as shown in FIG. 3). In the cracking unit 162, higher molecular weight hydrocarbons are cracked back to lighter hydrocarbons to form the synthetic crude oil 164. The cracking unit 162 may include any suitable cracking operation. A preferred cracking method is hydrocracking, in which case hydrogen 174 is added to the cracking until 162 so that the synthetic crude oil 164 will be a highly saturated. The hydrogen for the hydrocracking process may be obtained by separating out a small amount of hydrogen from the synthesis gas 108 (as shown in FIGS. 1 through 3) prior to introduction of the synthesis gas 108 into the Fischer-Tropsch reactors. This could be done by simple membrane separation. When removing hydrogen from the synthesis gas, it is important that the synthesis gas 108 be generated to be somewhat more rich in hydrogen than desired for feed to the Fischer-Tropsch reactors, so that after the hydrogen removal, the synthesis gas 108 will have the desired $H_2/CO$ feed ratio to balance with the $H_2/CO$ consumption ratio, as discussed above. An even more preferred embodiment would involve a cracking unit that consists of a combined hydrocracker/isomerization unit, so that a larger degree of hydrocarbon branching will be present in the synthetic crude oil 164.

While various embodiments of the present invention have been described in detail, it is apparent that further combinations, modifications and adaptations of the invention will occur to those skilled in the art. For example, any of the features disclosed in or discussed in connection with any of FIGS. 1–3 may be combined in any compatible combination with any other features disclosed in or discussed in connection with any of FIGS. 1–3. Furthermore, the product upgrading of FIG. 4 may be combined with any of the staged hydrocarbon synthesis flow diagrams shown in any one of FIGS. 1–3. It is to be expressly understood that such combinations, modifications and adaptations are within the spirit and scope of the present invention. It is further intended that the claims appended hereto be interpreted to extend to the maximum extent permitted by the prior art.

What is claimed is:

1. A staged Fischer-Tropsch method for synthesizing hydrocarbons, comprising:

generating a synthesis gas from a gaseous hydrocarbon feed, with hydrocarbons in the gaseous hydrocarbon feed including greater than about 95% by moles of $C_4$-hydrocarbons, the synthesis gas including at least carbon monoxide, hydrogen and carbon dioxide, with the hydrogen and carbon monoxide being present in the synthesis gas at a molar feed ratio of hydrogen to carbon monoxide in a range of from about 1.3 to about 1.9;

feeding the synthesis gas to a plurality of Fischer-Tropsch reactor stages arranged in series, each of said Fischer-Tropsch reactor stages having a reactor volume containing a Fischer-Tropsch catalyst; and reacting in a staged Fischer-Tropsch reaction at least a portion of the synthesis gas in each of the Fischer-Tropsch reactor stages, with intermediate removal of water between the Fischer-Tropsch reactor stages, to form Fischer-Tropsch reaction products including synthesized hydrocarbon products and carbon dioxide, the Fischer-Tropsch catalyst being an iron-based catalyst contained in the reactor volume of each of the Fischer-Tropsch reactor stages in the form of particles slurried with hot liquid hydrocarbons of the Fischer-Tropsch reaction products;

wherein carbon dioxide is added as feed to the step of generating the synthesis gas and at least the first one in series of the Fischer-Tropsch reactor stages is operated at a carbon monoxide conversion of no larger than 70%, so that the overall consumption of the hydrogen and carbon monoxide across all of the series of Fischer-Tropsch reactor stages is at an overall molar consumption ratio of hydrogen to carbon monoxide having a value in a range of from about 0.2 smaller than the molar feed ratio to about 0.2 larger than the molar feed ratio.

2. The method of claim 1, wherein the carbon monoxide conversion in at least each of the first two in series of the Fischer-Tropsch reactor stages is smaller than 70%.

3. The method of claim 2, wherein the plurality of Fischer-Tropsch reactor stages includes at least three said Fischer-Tropsch reactor stages in series, at least each of the first three in series of the Fischer-Tropsch reactor stages being operated at a carbon monoxide conversion of smaller than 70%.

4. The method of claim 1, wherein at least the first one in series of the Fischer-Tropsch reactor stages is operated at a carbon monoxide conversion of smaller than about 65%.

5. The method of claim 4, wherein the overall conversion of carbon monoxide to the Fischer-Tropsch reaction products across all of the series of Fischer-Tropsch reactor stages is larger than about 85%.

6. The method of claim 1, wherein at least the first one in series of the Fischer-Tropsch reactor stages is operated at a carbon monoxide conversion of smaller than about 60%.

7. The method of claim 6 wherein at least each of the first two in series of the Fischer-Tropsch reactor stages is operated at a carbon monoxide conversion of from about 40% to about 60%.

8. The method of claim 1, wherein the reactor volume of a first one in series of the Fischer-Tropsch reactor stages is larger than the reactor volume of a second one in series of the Fischer-Tropsch reactor stages.

9. The method of claim 8, wherein the reactor volume of the second one in series of the Fischer-Tropsch reactor stages is no larger than about 70% of the reactor volume of the first one in series of the Fischer-Tropsch reactor stages.

10. The method of claim 1, wherein the catalyst is a supported iron-based catalyst, including iron supported on a support material.

11. The method of claim 10, wherein the support material comprises alumina.

12. The method of claim 10, wherein the support material comprises silica.

13. The method of claim 10, wherein the support material comprises carbon.

14. The method of claim 10, wherein the particles have a size of from about 50 microns to about 200 microns.

15. The method of claim 1, wherein the catalyst is an unsupported iron catalyst having a size of smaller than about 60 microns.

16. The method of claim 1, wherein:

during the step of reacting, gaseous effluent is removed from each of the Fischer-Tropsch reactor stages, the gaseous effluent including at least some carbon monoxide, hydrogen, carbon dioxide and water;

at least a portion of the gaseous effluent removed from each of the Fischer-Tropsch reactor stages, except for the last one in series of the Fischer-Tropsch reactor stages, is introduced into the next succeeding Fischer-Tropsch reactor stage, with the intermediate removal of water between the Fischer-Tropsch reactor stages comprising removing at least a portion of the water from the gaseous effluent prior to introduction into the next succeeding of the Fischer-Tropsch reactor stages; and the carbon dioxide added as feed to the step of generating the synthesis gas comprises at least a portion of the carbon dioxide of the gaseous effluent from the last one in series of the Fischer-Tropsch reactor stages.

17. The method of claim 16, wherein carbon dioxide in noncondensible gases of the gaseous effluent is not removed from the gaseous effluent between the Fischer-Tropsch reactor stages.

18. The method of claim 1, wherein the gaseous hydrocarbon feed comprises gaseous hydrocarbon components from at least one of natural gas and petroleum gas.

19. The method of claim 1, wherein the overall molar consumption ratio has a value in a range of from about 0.15 smaller than the molar feed ratio to about 0.15 larger than the molar feed ratio.

20. The method of claim 1, wherein the overall molar consumption ratio has a value in a range of from about 0.1 smaller than the molar feed ratio to about 0.1 larger than the molar feed ratio.

21. The method of claim 1, wherein each of the molar feed ratio and the overall molar consumption ratio is in a range of from about 1.4 to about 1.9.

22. The method of claim 1, wherein each of the molar feed ratio and the overall molar consumption ratio is in a range of from about 1.5 to about 1.8.

23. The method of claim 17, wherein the carbon dioxide added as feed to the step of generating the synthesis gas is obtained substantially entirely from the gaseous effluent from the last one in series of the Fischer-Tropsch reactor stages.

24. The method of claim 1, wherein oxygen gas is added as feed to the step of generating the synthesis gas.

25. The method of claim 24, wherein steam is added as feed to the step of generating the synthesis gas, to at least partially assist in control of the relationship between the molar feed ratio and the molar consumption ratio.

26. The method of claim 1, wherein:

the $C_5+$ portion of the hydrocarbon products include at least about 90% of the carbon contained in the hydrocarbons of the gaseous hydrocarbon feed.

27. The method of claim 1, wherein:

the $C_5+$ portion of the hydrocarbon products have a total heating value of at least about 65% of the total heating value of the hydrocarbons of the gaseous hydrocarbon feed.

28. The method of claim 1, wherein at least a portion of the hydrocarbon products are subjected to a cracking operation to prepare a synthetic crude oil.

29. The method of claim 28, wherein at least a portion of synthetic crude oil is distilled to form at least one distillate product.

30. The method of claim 29, wherein the at least one distillate product includes at least one of a diesel range distillate product, a jet fuel range distillate product and a naphtha range distillate product.

31. The method of claim 29, wherein at least a portion of the distillate product is blended with a refined petroleum product.

32. The method of claim 1, wherein at least a portion of the hydrocarbon products are converted to a purified wax product.

33. The method of claim 1, wherein the plurality of Fischer-Tropsch reactor stages includes at least three of the Fischer-Tropsch reactor stages arranged in series, each of at least two of the Fischer-Tropsch reactor stages being operated at a carbon monoxide conversion of from about 40% to about 65%.

34. The method of claim 33, wherein at least the first one in series of the Fischer-Tropsch reactor stages is operated at a carbon monoxide conversion of from about 40% to about 60%.

35. The method of claim 1, wherein the step of generating the synthesis gas comprises partial oxidation of the gaseous hydrocarbon feed in the presence of the carbon dioxide added as feed.

36. The method of claim 1, wherein each of the molar feed ratio and the overall molar consumption ratio is in a range of from about 1.3 to about 1.9.

* * * * *

UNITED STATES PATENT AND TRADEMARK OFFICE
CERTIFICATE OF CORRECTION

PATENT NO. : 6,156,809  
DATED : December 5, 2000  
INVENTOR(S) : Clark et al.

Page 1 of 1

It is certified that error appears in the above-identified patent and that said Letters Patent is hereby corrected as shown below:

<u>Claim 1, column 14,</u>  
Line 51, delete " $C_4$-hydrocarbons" and insert therefor -- $C_4$- hydrocarbons --

*please note addition of space.

Signed and Sealed this

Thirtieth Day of October, 2001

*Attest:*

NICHOLAS P. GODICI  
*Attesting Officer*    *Acting Director of the United States Patent and Trademark Office*